United States Patent
Matsuoka et al.

(10) Patent No.: US 10,094,756 B2
(45) Date of Patent: Oct. 9, 2018

(54) PARTICULATE MEASUREMENT SYSTEM

(71) Applicant: NGK SPARK PLUG CO., LTD., Nagoya-shi, Aichi (JP)

(72) Inventors: Toshiya Matsuoka, Kaizu (JP); Takeshi Sugiyama, Ichinomiya (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 359 days.

(21) Appl. No.: 14/872,447

(22) Filed: Oct. 1, 2015

(65) Prior Publication Data

US 2016/0103054 A1 Apr. 14, 2016

(30) Foreign Application Priority Data

Oct. 7, 2014 (JP) ................................. 2014-206387
Sep. 29, 2015 (JP) ................................. 2015-190528

(51) Int. Cl.
*G01N 15/06* (2006.01)
*G01N 15/00* (2006.01)
*G01M 15/10* (2006.01)

(52) U.S. Cl.
CPC ...... *G01N 15/0656* (2013.01); *G01M 15/102* (2013.01); *G01N 15/0606* (2013.01); *G01N 2015/0046* (2013.01)

(58) Field of Classification Search
CPC ....... G01N 15/0656; G01N 2015/0046; G01N 15/0606
USPC .................................. 73/23.33, 23.21, 28.01
See application file for complete search history.

(56) References Cited

U.S. PATENT DOCUMENTS

| 7,224,455 | B2 * | 5/2007 | Myers .................... G01N 21/53 356/337 |
| 2012/0285219 | A1 * | 11/2012 | Matuoka ............. F02D 41/1466 73/23.33 |
| 2012/0304738 | A1 | 12/2012 | Landkammer |
| 2014/0069169 | A1 | 3/2014 | Janka |
| 2015/0120229 | A1 | 4/2015 | Sugiyama et al. |
| 2017/0307501 | A1 * | 10/2017 | Shimokawa ....... G01N 15/0806 |

FOREIGN PATENT DOCUMENTS

| JP | 2013-520669 A | 6/2013 |
| JP | 2014-501391 A | 1/2014 |
| JP | 2015-108620 A | 6/2015 |

* cited by examiner

*Primary Examiner* — R. A. Smith
*Assistant Examiner* — John M Royston
(74) *Attorney, Agent, or Firm* — Sughrue Mion, PLLC

(57) ABSTRACT

A particulate measurement system includes an ion generation section for generating ions by means of corona discharge; an electrification chamber for electrifying particulates contained in a gas under measurement; a measurement signal generation circuit for generating a measurement signal which correlates with the amount of the particulates; and a particulate amount determination section for determining the amount of the particulates. The particulate measurement system further includes a particle diameter estimation section for estimating the particle diameter of the particulates contained in the gas under measurement. The particulate amount determination section performs correction by multiplying the measurement signal or the amount of the particulates determined from the measurement signal by a coefficient relating to the ratio between the estimated particle diameter and a reference particle diameter.

5 Claims, 8 Drawing Sheets

PARTICULATE MEASUREMENT SYSTEM

TECHNICAL FIELD

The present invention relates to a particulate measurement system which measures the amount of particulates such as soot contained in a gas.

BACKGROUND ART

Conventionally, there has been known a particulate measurement system which measures the amount of particulates such as soot contained in exhaust gas discharged from an internal combustion engine such as a diesel engine (Patent Documents 1 and 2). This particulate measurement system generates ions by means of corona discharge, electrifies particulates contained in the exhaust gas by means of the generated ions, captures ions not used for the electrification of particulates, and measures the amount of particulates contained in the exhaust gas on the basis of the amount of trapped ions (in other words, on the basis of the amount of ions used for the electrification of particulates and not trapped). The amount of trapped ions correlates with the amount of ions used for the electrification, and the amount of ions used for the electrification correlates with the amount of particulates contained in the exhaust gas. Therefore, the particulate measurement system can measure the amount of particulates contained in the exhaust gas flow from the amount of trapped ions.

PRIOR ART DOCUMENTS

Patent Documents

[Patent Document 1] Japanese Kohyo (PCT) Patent Publication No. 2013-520669
[Patent Document 2] Japanese Kohyo (PCT) Patent Publication No. 2014-501391

SUMMARY OF THE INVENTION

Problem to be Solved by the Invention

However, the present inventors found a new problem that since the relation between the amount of particulates and a measurement signal representing the current value of current corresponding to the above-described amount of ions changes considerably due to the influence of difference in particle diameter of particulates such as soot, measurement accuracy is low.

Means for Solving the Problem

In order to solve the above-described problem, the present invention can be realized in the following modes.
(1) According to one mode of the present invention, there is provided a particulate measurement system comprising an ion generation section for generating ions by means of corona discharge; an electrification chamber for electrifying, by using the ions, at least a portion of particulates contained in a gas under measurement; an ion trapping section for trapping at least a portion of the ions which have not been used for the electrification of the particulates; a measurement signal generation circuit for generating a measurement signal which correlates with the amount of the particulates contained in the gas under measurement on the basis of a current value corresponding to a difference between the amount of the ions generated from the ion generation section and the amount of the ions captured by the ion trapping section; and a particulate amount determination section for determining the amount of the particulates contained in the gas under measurement on the basis of the measurement signal. The particulate measurement system further comprises a particle diameter estimation section for estimating the particle diameter of the particulates contained in the gas under measurement, wherein the particulate amount determination section performs correction by multiplying the measurement signal or the amount of the particulates determined from the measurement signal by a coefficient relating to a ratio between the estimated particle diameter and a reference particle diameter. According to the particulate measurement system of this mode, the measurement signal or the particulate amount determined from the measurement signal is corrected by multiplying the measurement signal or the particulate amount by the coefficient relating to the ratio between the estimated particle diameter and the reference particle diameter. Therefore, the influence of a variation due to the difference of the particle diameter on the relation between the measurement signal and the particulate amount can be reduced, whereby the measurement accuracy of the particulate amount can be improved.
(2) In the above-described particulate measurement system, the particulate amount determination section may determine, as the amount of the particulates, the mass concentration of the particulates by performing the correction in accordance with an expression of $y = y_0 \times (B/A)^N$, where $y$ is the measurement signal or the mass concentration of the particulates after the correction, $y_0$ is the measurement signal or the mass concentration of the particulates before the correction, A is the reference particle diameter, B is the estimated particle diameter, and N is an integer of 2 or greater.

According to this configuration, the measurement accuracy of the mass concentration of particulates can be improved by merely performing the correction in accordance with the above-described expression. Notably, when N is 2, the measurement accuracy of the mass concentration of particulates can be improved to a sufficient degree by using a simple computation expression.
(3) In the above-described particulate measurement system, the particulate amount determination section may determine, as the amount of the particulates, the number concentration of the particulates by performing the correction in accordance with an expression of $y = y_0 \times (A/B)$, where $y$ is the measurement signal or the number concentration of the particulates after the correction, $y_0$ is the measurement signal or the number concentration of the particulates before the correction, A is the reference particle diameter, and B is the estimated particle diameter.

According to this configuration, the measurement accuracy of the number concentration of particulates can be improved by merely performing the correction in accordance with the above-described expression.
(4) In the above-described particulate measurement system, the particulate measurement system may measure the amount of the particulates contained in exhaust gas discharged from an internal combustion engine of a vehicle.

According to this configuration, the accuracy in measuring the amount of particulates contained in the exhaust gas discharged from the internal combustion engine of the vehicle can be improved, whereby deterioration and/or anomaly of a filter apparatus for trapping the particulates contained in the exhaust gas can be detected accurately.

(5) In the above-described particulate measurement system, the particle diameter estimation section may estimate the particle diameter on the basis of a parameter relating to drive of the internal combustion engine.

The parameter relating to drive of the internal combustion engine is considered to influence the particle diameter of the particulates contained in the exhaust gas. Therefore, according to this configuration, the estimation accuracy of the particle diameter can be increased, whereby the measurement accuracy of the particulate amount can be improved.

(6) In the above-described particulate measurement system, the particle diameter estimation section may estimate the particle diameter on the basis of a plurality of parameters different from one another.

According to this configuration, the estimation accuracy of the particle diameter can be improved as compared with a configuration in which the particle diameter is estimated on the basis of a single type of parameter, whereby the measurement accuracy of the particulate amount can be improved.

(7) In the above-described particulate measurement system, the plurality of parameters different from one another preferably include at least rotational speed of the internal combustion engine and fuel injection amount.

Since the rotational speed of the internal combustion engine and the fuel injection amount are considered to be particularly influential on the particle diameter of particulates contained in the exhaust gas, through use of these parameters, the measurement accuracy of the particulate amount is improved.

Notably, the present invention can be realized in various forms. For example, the present invention can be realized as a particulate sensor, a particulate detection method, an internal combustion engine including a particulate measurement system, or a vehicle including this internal combustion engine.

MODES FOR CARRYING OUT THE INVENTION

A. Embodiment
A-1. Configuration of Apparatus

Figure 1A:
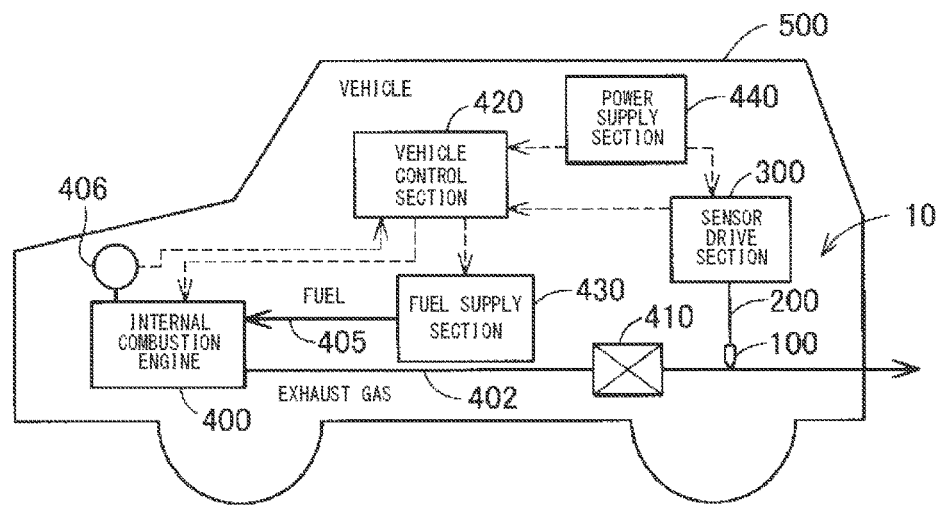
FIG. 1A and FIG. 1B are explanatory views schematically showing the structure of a vehicle to which a particulate measurement system according to one embodiment of the present invention is applied.
Figure 1B:
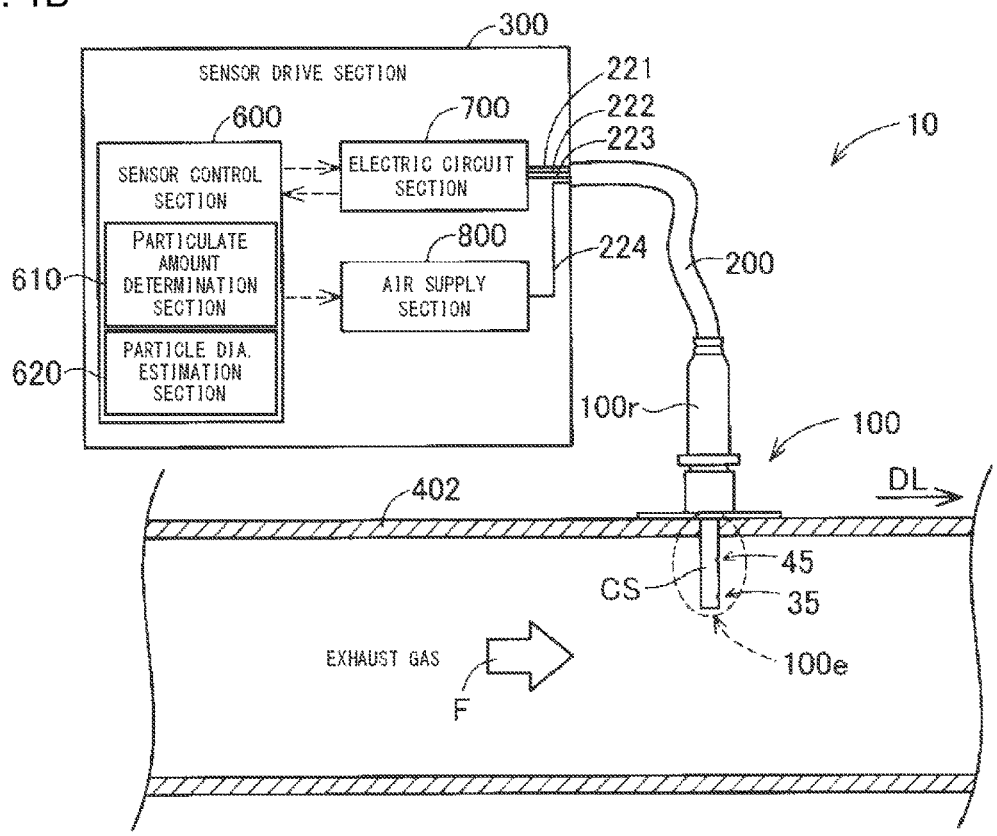

FIGS. 1A and 1B are a pair of explanatory views schematically showing the structure of a vehicle to which a particulate measurement system according to one embodiment of the present invention is applied. FIG. 1A is an explanatory view schematically showing an example of the structure of a vehicle 500 on which a particulate measurement system 10 is mounted. FIG. 1B is an explanatory view schematically showing the configuration of the particulate measurement system 10 attached to the vehicle 500. The particulate measurement system 10 includes a particulate sensor 100, a cable 200, and a sensor drive section 300, and measures the amount of particulates such as soot contained in exhaust gas (gas under measurement) discharged from an internal combustion engine 400. The internal combustion engine 400, which is a power source of the vehicle 500, is a diesel engine or the like.

The vehicle 500 has various types of sensors 406 provided at different locations within the vehicle 500 in addition to the particulate sensor 100. Measured values of parameters relating to drive of the internal combustion engine 400 are supplied from these sensors 406 to a vehicle control section 420. The parameters relating to drive of the internal combustion engine 400 have a broad concept which encompasses the operating condition parameters of the internal combustion engine 400 and an environmental parameter which changes with operation of the internal combustion engine 400. Examples of the operating condition parameters of the internal combustion engine 400 include the rotational speed of the internal combustion engine 400, the amount of injected fuel, the speed of the vehicle 500, the torque of the internal combustion engine 400, the exhaust pressure of the internal combustion engine 400, the intake pressure of the internal combustion engine 400, the EGR opening degree (in the case where an EGR valve (Exhaust Gas Recirculation valve) is provided), the amount of air taken into the internal combustion engine 400, the timing of ignition, etc. An example of the environmental parameter which changes with operation of the internal combustion engine 400 is the exhaust gas temperature of the internal combustion engine 400. Each of these parameters relating to drive of the internal combustion engine 400 is a parameter which is considered to affect the particle diameter of particulates contained in the exhaust gas.

The particulate sensor 100 is attached to an exhaust gas pipe 402 extending from the internal combustion engine 400, and is electrically connected to the sensor drive section 300 through the cable 200. In the present embodiment, the particulate sensor 100 is attached to the exhaust gas pipe 402 to be located downstream of a filter apparatus 410 (e.g., a DPF (diesel particulate filter)). The particulate sensor 100 outputs to the sensor drive section 300 a signal which correlates with the amount of particulates contained in the exhaust gas.

The sensor drive section 300 drives the particulate sensor 100 and measures the amount of particulates contained in the exhaust gas on the basis of the signal supplied from the particulate sensor 100. In the present embodiment, "the amount of particulates" is measured as "the mass concentration of particulates" which is proportional to the masses of particulates contained in a unit volume of the exhaust gas and as "the number concentration of particulates" which is proportional to the number of particulates contained in a unit volume of the exhaust gas. Notably, only one of "the mass concentration of particulates" and "the number concentration of particulates" may be measured. The sensor drive section 300 outputs to the vehicle control section 420 a signal representing the amount of particulates contained in the exhaust gas. In accordance with the signal supplied from the sensor drive section 300, the vehicle control section 420 controls the combustion state of the internal combustion engine 400, the amount of fuel supplied from a fuel supply section 430 to the internal combustion engine 400 through a fuel pipe 405, etc. The vehicle control section 420 may be configured to warn a driver of the vehicle 500 of deterioration or anomaly of the filter apparatus 410, for example, when the amount of particulates contained in the exhaust gas is greater than a predetermined upper limit (threshold). Electric power is supplied from a power supply section 440 to the sensor drive section 300 and the vehicle control section 420.

As shown in FIG. 1B, the particulate sensor 100 has a cylindrical forward end portion 100e, and is fixed to the outer surface of the exhaust gas pipe 402 such that the forward end portion 100e is inserted into the exhaust gas pipe 402. In the present embodiment, the forward end portion 100e of the particulate sensor 100 is inserted approximately perpendicular to an extension direction DL of the exhaust gas pipe 402. A casing CS of the forward end portion 100e has an inflow hole 45 and a discharge hole 35 formed on the surface of the casing CS. The inflow hole 45 is used to introduce the exhaust gas into the interior of the casing CS, and the discharge hole 35 is used to discharge the introduced exhaust gas to the outside of the casing CS. A portion of the exhaust gas flowing through the exhaust gas pipe 402 is introduced into the interior of the casing CS of the forward end portion 100e through the inflow hole 45. Particulates contained in the introduced exhaust gas are electrified by ions (positive ions in the present embodiment) generated by the particulate sensor 100. The exhaust gas containing the electrified particulates is discharged to the outside of the casing CS through the discharge hole 35. The internal structure of the casing CS and the specific structure of the particulate sensor 100 will be described later. Notably, in the drawing, the flow direction of the exhaust gas is indicated by an arrow F.

The cable 200 is attached to a rear end portion 100r of the particulate sensor 100. The cable 200 includes a first wiring line 221, a second wiring line 222, a signal line 223, and an air supply tube 224 bundled together. The first wiring line 221, the second wiring line 222, and the signal line 223 are electrically connected to an electric circuit section 700 which will be described later. The air supply tube 224 is connected to an air supply section 800 which will be described later.

The sensor drive section 300 includes a sensor control section 600, the electric circuit section 700, and the air supply section 800. Electrical connection is established between the sensor control section 600 and the electric circuit section 700 and between the sensor control section 600 and the air supply section 800.

The sensor control section 600 includes a microcomputer, and controls the electric circuit section 700 and the air supply section 800. Also, the sensor control section 600 includes a particulate amount determination section 610 and a particle diameter estimation section 620. The particulate amount determination section 610 determines the amount of particulates contained in the exhaust gas on the basis of a signal supplied from the electric circuit section 700. The particulate amount determination section 610 outputs to the vehicle control section 420 a signal representing the amount of particulates contained in the exhaust gas. The particle diameter estimation section 620 estimates the particle diameter of particulates contained in the exhaust gas. Specifically, as will be described later, the particle diameter estimation section 620 estimates the particle diameter of particulates on the basis of the signals relating to drive of the internal combustion engine 400 which are input to the vehicle control section 420 from the various sensors 406.

The electric circuit section 700 supplies electric power to the particulate sensor 100 through the first wiring line 221 and the second wiring line 222 so as to drive the particulate sensor 100. A signal which correlates with the amount of particulates contained in the exhaust gas is supplied from the particulate sensor 100 to the electric circuit section 700 through the signal line 223. Using this signal supplied through the signal line 223, the electric circuit section 700 outputs to the sensor control section 600 a signal corresponding to the amount of particulates contained in the exhaust gas. These signals will be described in detail later.

The air supply section 800 includes a pump (not shown), and supplies high-pressure air to the particulate sensor 100 through the air supply tube 224 in response to an instruction from the sensor control section 600. The high-pressure air supplied from the air supply section 800 is used for measurement of the amount of particulates by the particulate sensor 100. Notably, instead of supplying air from the air supply section 800, another type of gas may be supplied to the particulate sensor 100.

Figure 2:
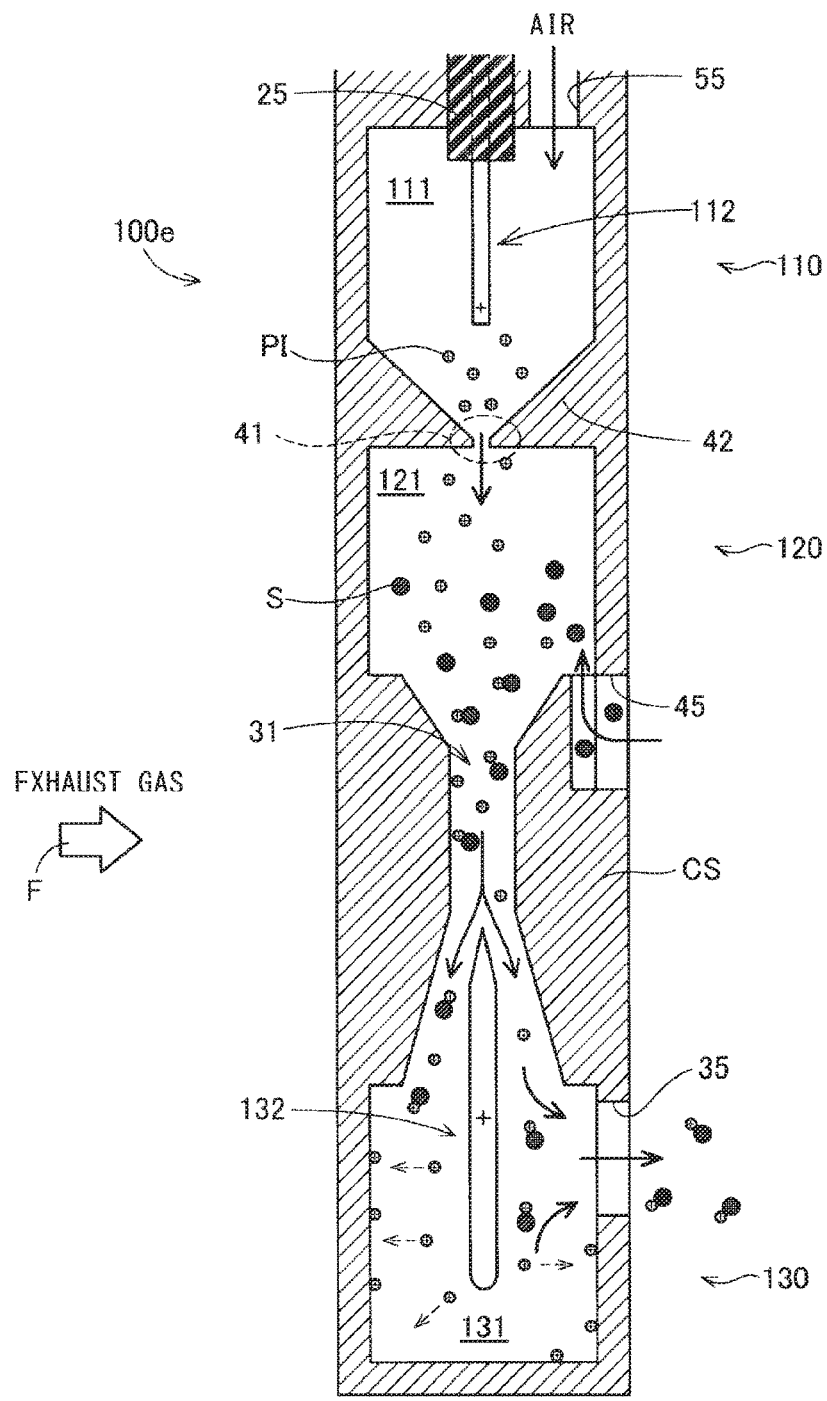
FIG. 2 is an explanatory view schematically showing the structure of a forward end portion 100e of a particulate sensor 100.

FIG. 2 is an explanatory view schematically showing the structure of the forward end portion 100e of the particulate sensor 100. The forward end portion 100e includes an ion generation section 110, an exhaust gas electrification section 120, and an ion trapping section 130 which are provided in the casing CS. Namely, within the casing CS, these three processing sections 110, 120, and 130 are arranged in this order, along the axial direction of the particulate sensor 100, from the base end side (the upper side in FIG. 2) of the forward end portion 100e toward the forward end side (the lower side in FIG. 2) thereof. The casing CS is formed of an electrically conductive material, and is connected to a secondary-side ground SGL (FIG. 3) through the signal line 223 (FIG. 1).

The ion generation section 110 is a processing section for generating ions (positive ions in the present embodiment) which are supplied to the exhaust gas electrification section 120. The ion generation section 110 includes an ion generation chamber 111 and a first electrode 112. The ion generation chamber 111 is a small space formed inside the casing CS. An air supply hole 55 and a nozzle 41 are provided on the inner circumferential surface of the ion generation chamber 111. The first electrode 112 is attached such that it projects into the ion generation chamber 111. The air supply hole 55 communicates with the air supply tube 224 (FIG. 1), and the high-pressure air supplied from the air supply section 800 (FIG. 1) is supplied to the ion generation chamber 111 through the air supply hole 55. The nozzle 41 is a very small hole (orifice) provided near the center of a partition wall 42 provided between the ion generation chamber 111 and the exhaust gas electrification section 120. The nozzle 41 supplies the ions generated in the ion generation chamber 111 to an electrification chamber 121 of the exhaust gas electrification section 120. The first electrode 112 has a rod-like outer shape, and its base end portion is fixed to the casing CS via a ceramic pipe 25 in a state in which a forward end portion of the first electrode 112 is located near the partition wall 42. The first electrode 112 is connected to the electric circuit section 700 (FIG. 1) through the first wiring line 221 (FIG. 1).

Using the electric power supplied from the electric circuit section 700, the ion generation section 110 applies a DC voltage (e.g., 2 to 3 kV) between the first electrode 112 (positive pole) and the partition wall 42 (negative pole). Through application of this voltage, the ion generation section 110 produces corona discharge between a forward end portion of the first electrode 112 and the partition wall 42 to thereby generate positive ions PI. The positive ions PI generated in the ion generation section 110 are jetted into the electrification chamber 121 of the exhaust gas electrification section 120 through the nozzle 41 together with the high-pressure air supplied from the air supply section 800 (FIG. 1). Preferably, the jetting speed of air jetted from the nozzle 41 is set to a speed near the speed of sound.

The exhaust gas electrification section 120 is a section for electrifying particulates S contained in the exhaust gas by positive ions PI, and includes the above-mentioned electrification chamber 121. The electrification chamber 121 is a small space located adjacent to the ion generation chamber 111, and communicates with the ion generation chamber 111 through the nozzle 41. Also, the electrification chamber 121 communicates with the outside of the casing CS through the inflow hole 45, and communicates with a trapping chamber 131 of the ion trapping section 130 through a gas flow passage 31. The electrification chamber 121 is configured such that, when air containing the positive ions PI are jetted from the nozzle 41, a negative pressure is created in the electrification chamber 121, and the exhaust gas located outside the casing CS flows into the electrification chamber 121 through the inflow hole 45. The air jetted from the nozzle 41 and containing the positive ions PI and the exhaust gas flowing inward through the inflow hole 45 are mixed together within the electrification chamber 121. At that time, at least a portion of the particulates S contained in the exhaust gas flowed inward through the inflow hole 45 are electrified by the positive ions PI supplied from the nozzle 41. The air containing the electrified particulates S and the positive ions PI not used for the electrification is supplied to the trapping chamber 131 of the ion trapping section 130 through the gas flow passage 31.

The ion trapping section 130 is a section for trapping ions not used for the electrification of the particulates S, and includes the above-mentioned trapping chamber 131 and a second electrode 132. The trapping chamber 131 is a small space located adjacent to the electrification chamber 121, and communicates with the electrification chamber 121 through the gas flow passage 31. Also, the trapping chamber 131 communicates with the outside of the casing CS through the discharge hole 35. The second electrode 132 has a generally rod-like outer shape and has a tapered upper end. The second electrode 132 is fixed to the casing CS such that its longitudinal direction coincides with the flow direction of air flowing through the gas flow passage 31 (the extending direction of the casing CS). The second electrode 132 is connected to the electric circuit section 700 (FIG. 1) through the second wiring line 222 (FIG. 1). The second electrode 132 functions as an auxiliary electrode to which a voltage of about 100 V is applied and which assists the operation of trapping positive ions not used for the electrification of particulates S. Specifically, a voltage is applied to the ion trapping section 130 such that the second electrode 132 serves as a positive pole, and the casing CS constituting the electrification chamber 121 and the trapping chamber 131 serves as a negative pole. As a result, the positive ions PI not used for the electrification of particulates S receive a repulsive force from the second electrode 132, whereby their advancing directions deviate to directions away from the second electrode 132. The positive ions PI whose advancing directions have been deviated are trapped by the inner circumferential walls of the trapping chamber 131 and the gas flow passage 31 which function as a negative pole. Meanwhile, the particulates S to which positive ions PI have adhered also receive the repulsive force from the second electrode 132 as in the case of the positive ions PI themselves. However, since the particulates S are larger in mass than the positive ions PI, the degree of deviation by the repulsive force is small as compared with the case of the positive ions PI themselves. Therefore, the electrified particulates S are discharged to the outside of the casing CS through the discharge hole 35 as a result of the flow of the exhaust gas.

The particulate sensor 100 outputs a signal showing a change in current which corresponds to the amount of positive ions PI trapped in the ion trapping section 130. The sensor control section 600 (FIG. 1) determines the amount of particulates contained in the exhaust gas on the basis of the signal output from the particulate sensor 100. A method of determining the amount of particulates contained in the exhaust gas on the basis of the signal output from the particulate sensor 100 will be described later.

Figure 3:
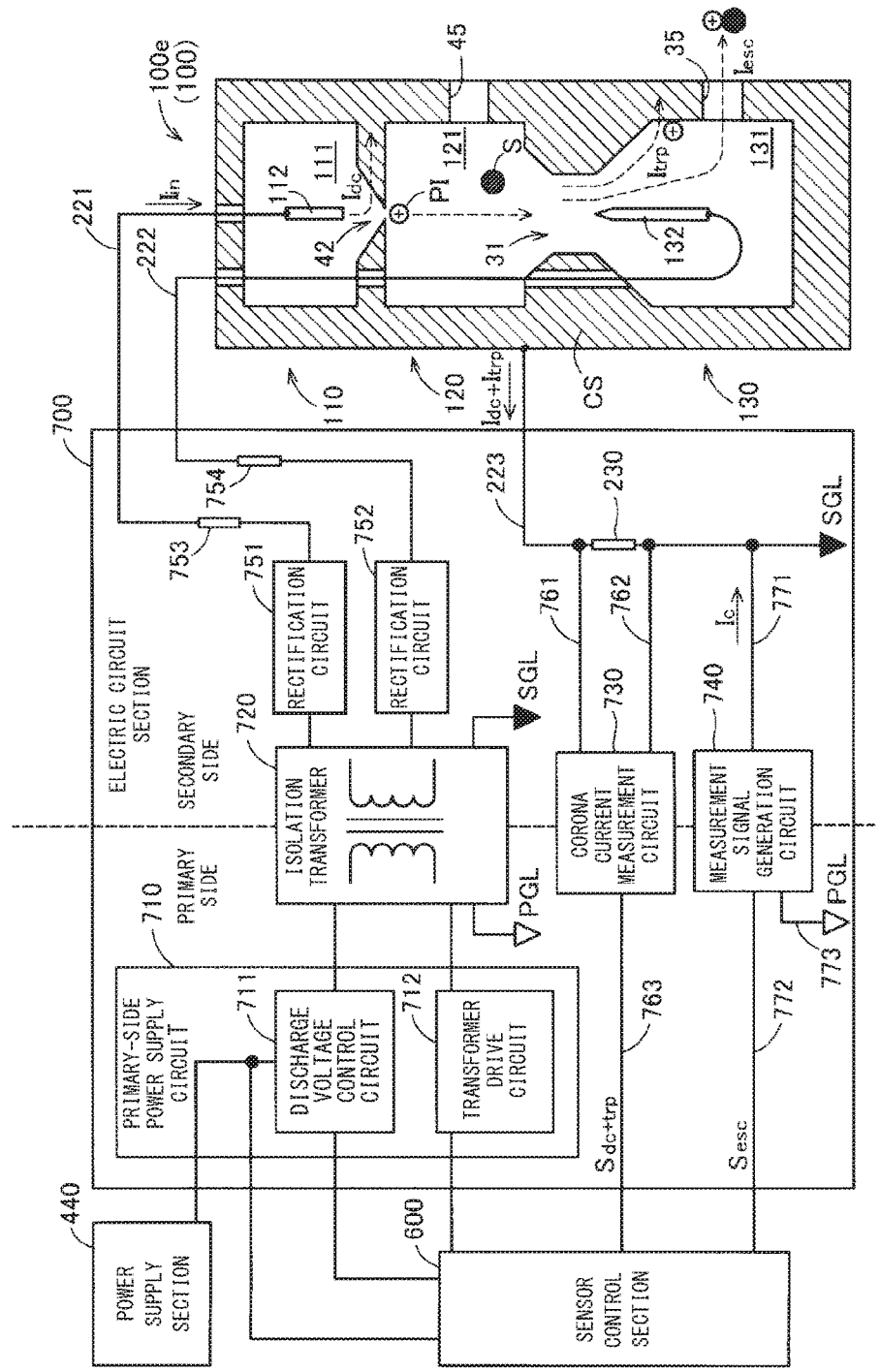
FIG. 3 is a block diagram schematically showing the configuration of an electric circuit section 700.

FIG. 3 is a block diagram schematically showing the configuration of the electric circuit section 700. The electric circuit section 700 includes a primary-side power supply circuit 710, an isolation transformer 720, a corona current measurement circuit 730, a measurement signal generation circuit 740, a first rectification circuit 751, and a second rectification circuit 752.

The primary-side power supply circuit 710 steps up a DC voltage supplied from the power supply section 440, supplies the stepped up voltage to the isolation transformer 720, and drives the isolation transformer 720. The primary-side power supply circuit 710 includes a discharge voltage control circuit 711 and a transformer drive circuit 712. The discharge voltage control circuit 711 includes a DC/DC converter. Under the control by the sensor control section 600, the discharge voltage control circuit 711 can arbitrarily change the voltage supplied to the isolation transformer 720. Control of the supplied voltage is substantially performed, for example, such that an input current $I_{in}$ supplied to the first electrode 112 of the particulate sensor 100 through the first wiring line 221 becomes equal to a target current (e.g., 5 μA). The method of this control will be described later. As a result, the amount of positive ions PI generated by the corona discharge in the ion generation section 110 can be made constant.

The transformer drive circuit 712 includes a switch circuit which can switch the flow direction of current flowing through the primary-side coil of the isolation transformer 720. The transformer drive circuit 712 drives the isolation transformer 720 by the switching operation of the switch circuit. In the present embodiment, the transformer drive circuit 712 is a push-pull circuit. However, the transformer drive circuit 712 may be other types of circuits such as a half bridge circuit and a full bridge circuit.

The isolation transformer 720 performs voltage conversion for the electric power supplied from the primary-side power supply circuit 710, and supplies the voltage-converted electric power (AC electric power in the present embodiment) to rectification circuits 751 and 752 on the secondary side. The configuration of the secondary-side coil allows the isolation transformer 720 to set different amplification factors for the electric power supplied to the first rectification circuit 751 and for the electric power supplied to the second rectification circuit 752. The isolation transformer 720 of the present embodiment is configured such that the primary-side coil and the secondary-side coil are not in physical contact with each other but are magnetically coupled with each other. A circuit on the primary side of the isolation transformer 720 includes the sensor control section 600 and the power supply section 440 as well as the primary-side power supply circuit 710. A circuit on the secondary side of the isolation transformer 720 includes the particulate sensor 100 and the rectification circuits 751 and 752. The corona current measurement circuit 730 and the measurement signal generation circuit 740 are provided between the circuit on the primary side of the isolation transformer 720 and the circuit on the secondary side of the isolation transformer 720, and are electrically connected to the primary-side and secondary-side circuits, respectively. As will be described later, the corona current measurement circuit 730 is configured such that a circuit portion electrically connected to the circuit on the primary side of the isolation transformer 720 is physically insulated from a circuit portion electrically connected to the circuit on the secondary side of the isolation transformer 720. Here, a ground (ground potential) which serves as a reference potential of the primary-side circuit is also referred to as a "primary-side ground PGL," and a ground which serves as a reference potential of the secondary-side circuit is also referred to as a "secondary-side ground SGL." An end of the primary-side coil of the isolation transformer 720 is connected to the primary-side ground PGL, and an end of the secondary-side coil thereof is connected to the secondary-side ground SGL. The casing CS of the particulate sensor 100 is connected to the secondary-side ground SGL through the signal line 223 and a shunt resistor 230.

Each of the rectification circuits 751 and 752 converts the AC electric power output from the isolation transformer 720 to a DC electric power. The first rectification circuit 751 is connected to the first electrode 112 of the particulate sensor 100 through the first wiring line 221 and a resistor 753 for short protection. The second rectification circuit 752 is connected to the second electrode 132 of the particulate sensor 100 through the second wiring line 222 and a resistor 754 for short protection.

The corona current measurement circuit 730 is connected to the opposite ends of the shunt resistor 230 on the signal line 223 through wiring lines 761 and 762, and is connected to the sensor control section 600 through a wiring line 763. The corona current measurement circuit 730 outputs to the sensor control section 600 a signal $S_{dc+trp}$ representing a current $(I_{dc}+I_{trp})$ flowing from the casing CS toward the secondary-side ground SGL through the signal line 223. Here, a "signal representing a current" is not limited to a signal which directly represents the current, and may be a signal which indirectly represents the current. For example, the "signal representing a current" may be a signal on the basis of which the current can be specified by applying a computation expression or a map to information obtained from the signal.

In accordance with the signal $S_{dc+trp}$ supplied from the corona current measurement circuit 730, the sensor control section 600 controls the discharge voltage control circuit 711. The outline of the control of the discharge voltage control circuit 711 by the sensor control section 600 will be described later.

The measurement signal generation circuit 740 measures a current $I_c$ which corresponds to the current $I_{esc}$ of positive ions PI which have flowed to the outside without being trapped in the ion trapping section 130 (hereinafter referred to as a "leak current $I_{esc}$"). The measurement signal generation circuit 740 is connected to the signal line 223 on the secondary side through a wiring line 771, and is connected to the sensor control section 600 on the primary side through a wiring line 772. Also, the measurement signal generation circuit 740 is connected to the primary-side ground PGL through a wiring line 773. The measurement signal generation circuit 740 outputs a measurement signal $S_{esc}$ to the sensor control section 600. Notably, the measurement signal generation circuit 740 may generate a low-sensitivity measurement signal and a high-sensitivity measurement signal and output these measurement signals to the sensor control section 600. In this case, one of the low-sensitivity measurement signal and the high-sensitivity measurement signal may be the measurement signal $S_{esc}$.

Currents flowing through the forward end portion 100e of the particulate sensor 100 satisfy the following relational expression (1).

$$I_{in}=I_{dc}+I_{trp}+I_{esc} \quad (1)$$

In this expression, $I_{in}$ is a current input to the first electrode 112, $I_{dc}$ is a discharge current flowing to the casing CS through the partition wall 42, $I_{trp}$ is a trap current corresponding to the amount of charge of positive ions PI trapped by the casing CS, and $I_{esc}$ is a leak current corresponding to the amount of charge of positive ions PI having flowed to the outside without being trapped in the ion trapping section 130.

Since the discharge current $I_{dc}$ and the trap current $I_{trp}$ flow from the casing CS to the secondary-side ground SGL through the signal line 223, a current $(I_{dc}+I_{trp})$ which is the sum of these currents flows through the shunt resistor 230 on the signal line 223. The current value of $(I_{dc}+I_{trp})$ is approximately equal to the current value of the input current $I_{in}$. This is because the leak current $I_{esc}$ in the expression (1) is about one millionth of the current $(I_{dc}+I_{trp})$ flowing through the signal line 223, and the leak current $I_{esc}$ can be substantially ignored when a variation in the in the input current $I_{in}$ is monitored. Since the current value of the input current $I_{in}$ and the current value of the corona current of the ion generation section 110 are equal to each other, it can be said that the current value of the current $(I_{dc}+I_{trp})$ flowing through the signal line 223 is approximately equal to the current value of the corona current. Therefore, it can be said that the corona current measurement circuit 730 outputs to the sensor control section 600 a signal $S_{dc+trp}$ which shows the current value of the corona current of the ion generation section 110. In view of this, the sensor control section 600 controls the discharge voltage control circuit 711 in accordance with the signal $S_{dc+trp}$ input from the corona current measurement circuit 730 such that the current value of the input current $I_{in}$ becomes equal to the target current value.

The leak current $I_{esc}$ is equal to the difference between the input current $I_{in}$ and the current $(I_{dc}+I_{trp})$ flowing through the shunt resistor 230.

$$I_{esc}=I_{in}-I_{dc}+I_{trp}) \quad (2)$$

A current $I_c$ corresponding to the leak current $I_{esc}$ flows through the measurement signal generation circuit 740. The measurement signal generation circuit 740 produces a measurement signal $S_{esc}$ corresponding to the current $I_c$ and outputs the measurement signal $S_{esc}$ to the sensor control section 600. The particulate amount determination section 610 of the sensor control section 600 determines the amount of particulates contained in the exhaust gas on the basis of the measurement signal $S_{esc}$. At that time, the particulate amount determination section 610 performs correction which will be described below.

A-2. Example of Configuration of Measurement Signal Generation Circuit

Figure 4:
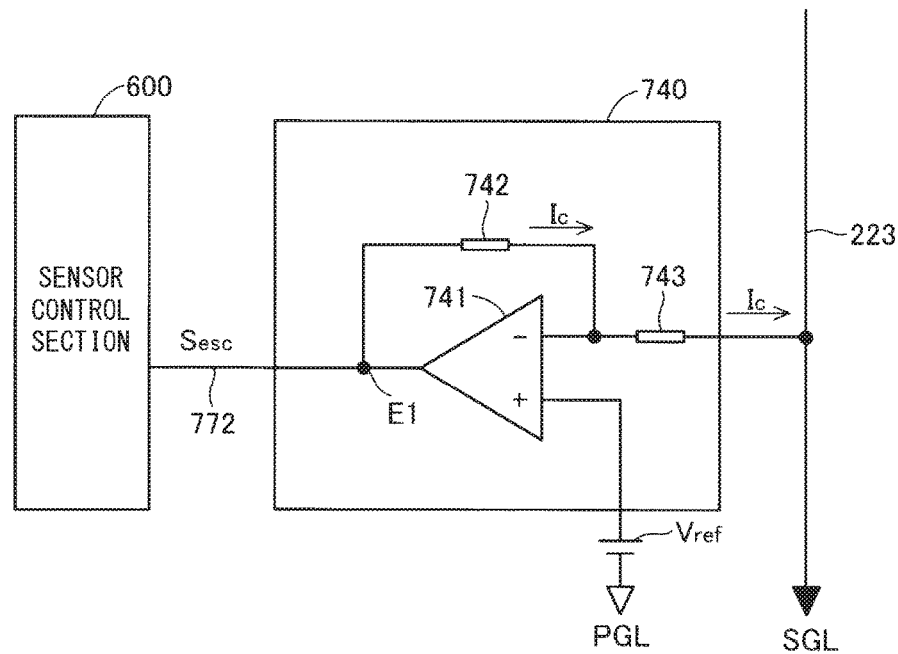
FIG. 4 is a block diagram showing the configuration of a measurement signal generation circuit 740.

FIG. 4 is a block diagram showing the configuration of the measurement signal generation circuit 740. The measurement signal generation circuit 740 includes an amplification circuit 741, a negative feedback resistor 742, and a resistor 743. An operational amplifier can be used as the amplification circuit 741. The inverting input terminal of the amplification circuit 741 is connected to the secondary-side ground SGL through the resistor 743 and the signal line 223. As shown in FIG. 3, this signal line 223 is connected to the casing CS of the particulate sensor. A power source $V_{ref}$ which provides a fixed reference voltage (e.g., 0.5 V) in relation to the primary-side ground PGL is connected to the non-inverting input terminal of the amplification circuit 741. In the following description, the same symbol "$V_{ref}$" is used so as to represent the reference voltage of this power source $V_{ref}$. By inputting the reference voltage $V_{ref}$ to the non-inverting input terminal of the amplification circuit 741, the potential difference between the two input terminals of the amplification circuit 741 can be adjusted such that the potential difference approaches a potential difference range within which errors (e.g., errors caused by bias current and offset voltage) are less likely to be produced. As will be described in detail later, the current $I_c$ corresponding to the leak current $I_{esc}$ (FIG. 3) of the particulate sensor 100 flows to the inverting input terminal of the amplification circuit 741. This current $I_c$ is converted to a voltage E1 by the amplification circuit 741. A signal $S_{esc}$ representing the voltage $E_1$ is supplied, as a measurement signal, to the sensor control section 600 through the wiring line 772.

The reason why the current $I_c$ flowing to the inverting input terminal of the amplification circuit 741 corresponds to the leak current $I_{esc}$ of the particulate sensor 100 is as follows. When the leak current $I_{esc}$ is generated, the reference potential of the secondary-side ground SGL becomes lower than the reference potential of the primary-side ground PGL in accordance with the magnitude of the leak current $I_{esc}$ This is because a difference in energy corresponding to the leak current $I_{esc}$ is produced between the energy (electric power) supplied from the primary-side circuit (including the primary-side power supply circuit 710 (FIG. 3)) to the particulate sensor 100 and the energy (electric power) output from the particulate sensor 100 through the signal line 223. When a difference is produced between the reference potential of the secondary-side ground SGL and the reference potential of the primary-side ground PGL as a result of generation of the leak current $I_{esc}$ the compensation current $I_c$ corresponding to this difference flows to the inverting input terminal of the amplification circuit 741. This compensation current $I_c$ is a current whose current value is equal to that of the leak current $I_{esc}$ and which compensates the difference between the reference potential of the secondary-side ground SGL and the reference potential of the primary-side ground PGL. Accordingly, the measurement signal generation circuit 740 can produce the voltage $E_1$ (and the measurement signal $S_{esc}$) representing the leak current $I_{esc}$ by means of I-V conversion of the compensation current $I_c$.

The output voltage E1 of the amplification circuit 741 is given by the following expression (3).

$$E1 = I_c \times R1 + V_{ref} \quad (3)$$

In the above expression, $I_c$ is the compensation current, R1 is the resistance of the negative feedback resistor 742, and $V_{ref}$ is the reference voltage of the amplification circuit 741.

The sensor control section 600 determines the amount of particulates contained in the exhaust gas on the basis of the measurement signal $S_{esc}$ supplied from the measurement signal generation circuit 740. In order to determine the amount of particulates contained in the exhaust gas from the measurement signal $S_{esc}$, for example, there can be used a method of referring to a map which shows the relation between the voltage value of the measurement signal $S_{esc}$ and the amount of particulates contained in the exhaust gas or a method of using a relational expression which shows the relation between the voltage value of the measurement signal $S_{esc}$ and the amount of particulates contained in the exhaust gas. The sensor control section 600 converts the voltage value of the measurement signal $S_{esc}$, which is analog, to a digital value of a predetermined resolution (for example, 8 bits).

A-3. Estimation of Particle Diameter

Figure 5:
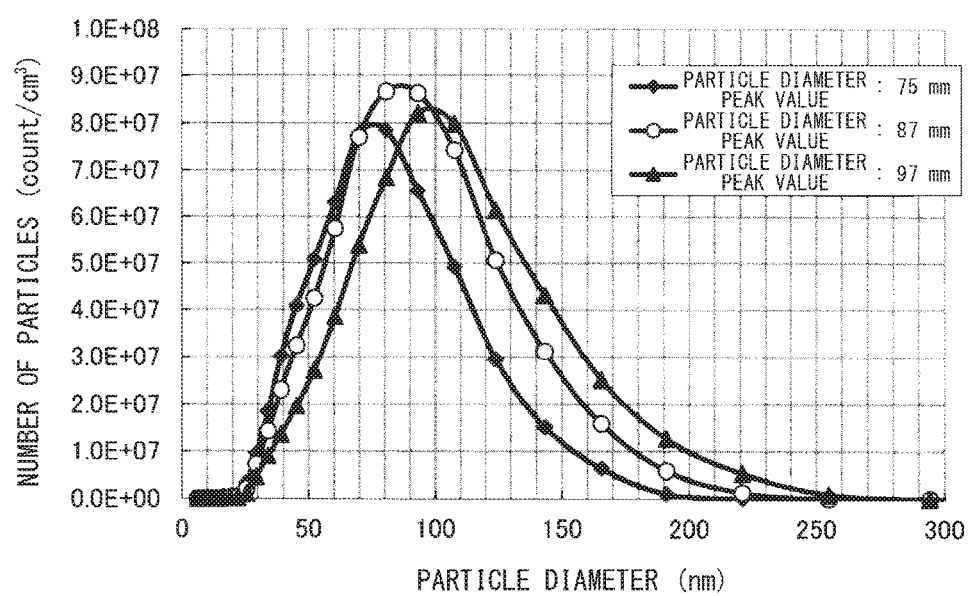
FIG. 5 is a graph showing an example of the particle diameter distribution of particulates S contained in exhaust gas.

FIG. 5 is a graph showing an example of the particle diameter distribution of particulates S contained in the exhaust gas. The horizontal axis represents the particle diameter (diameter) (nm) of particulates, and the vertical axis represents the number of particulates (count/cm³). The particle diameters of particulates S contained in the exhaust gas are not the same and exhibit a bell-shaped distribution curve in which the number of particulates becomes the maximum at a certain particle diameter. The particle diameter distribution of particulates S changes with the operating condition of the internal combustion engine 400 and the particle diameter peak value also changes accordingly. FIG. 5 shows the particle diameter distributions of particulates S for three cases where the internal combustion engine 400 is operated under three different sets of conditions, respectively. The particle diameter peak values of particulates S under the three different sets of conditions are 75 nm, 87 nm, and 97 nm, respectively.

In the present embodiment, the "particle diameter peak value" means the value of the particle diameter at which the number of particulates is the largest in the particle diameter distribution of particulates S contained in the exhaust gas when the internal combustion engine 400 is operated under predetermined operating conditions (the rotational speed of the internal combustion engine 400, the fuel injection amount, etc.). Also, in the present embodiment, the particle diameter peak value corresponds to the particle diameter in claims.

The particle diameter estimation section 620 estimates the particle diameter peak value of particulates S on the basis of the parameters relating to drive of the internal combustion engine 400 which are input to the vehicle control section 420 from the various sensors 406. In the present embodiment, the rotational speed of the internal combustion engine 400 and the fuel injection amount are used as the parameters relating to drive of the internal combustion engine 400, because it is considered that these parameters are particularly influential on the particle diameter of particulates S contained in the exhaust gas.

Figure 6:
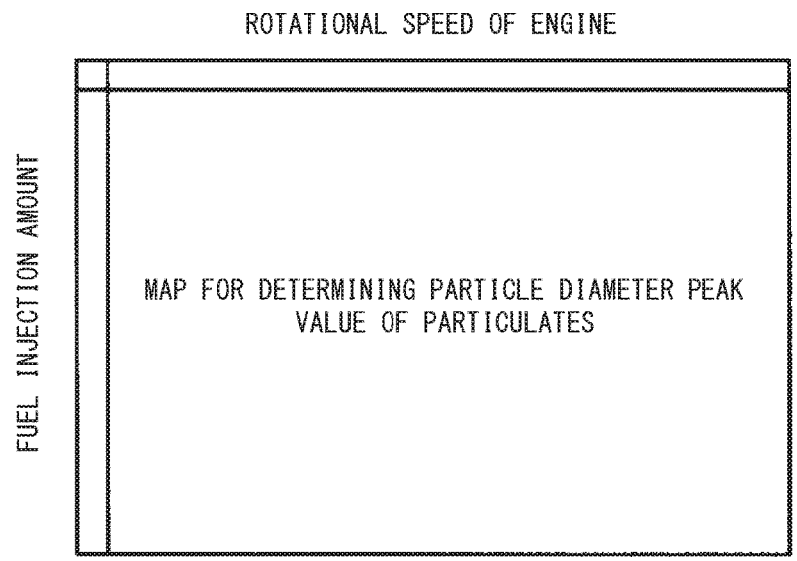
FIG. 6 is an explanatory illustration showing an example of a particle diameter peak value map.

FIG. 6 is an explanatory illustration showing an example of a particle diameter peak value map. The map shown in FIG. 6 shows the relation between the particle diameter peak value of particulates S and the rotational speed of the internal combustion engine 400 and the fuel injection amount. In the present embodiment, the particle diameter estimation section 620 estimates the particle diameter peak value of particulates S contained in the exhaust gas by referring to the two-dimensional map as shown in FIG. 6. Notably, in place of the map, a relational expression which shows the relation between the particle diameter peak value of particulates S contained in the exhaust gas and the rotational speed of the internal combustion engine 400 and the fuel injection amount may be used.

A-4. Correction of Measurement Results by Operating Conditions

A-4-1. Correction of Mass Concentration of Particulates

Figure 7:
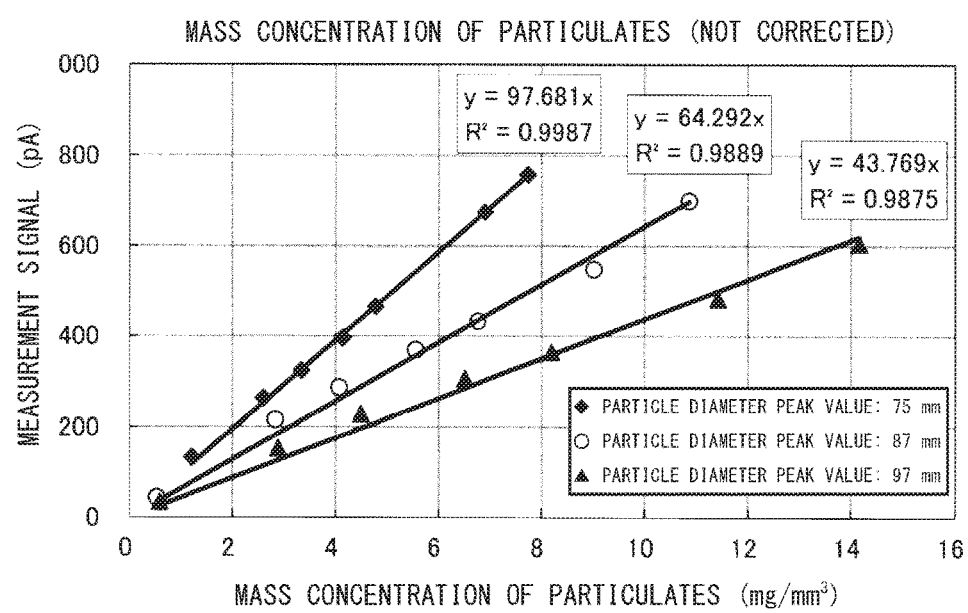
FIG. 7 is a graph showing an example of the relation between a measurement signal and the mass concentration of particulates S contained in exhaust gas.

FIG. 7 is a graph showing an example of the relation between the measurement signal and the mass concentration of particulates S contained in the exhaust gas. The horizontal axis represents the mass concentration (mg/m$^3$) of particulates S contained in the exhaust gas, and the vertical axis represents the measurement signal $S_{esc}$. To be precise, the vertical axis represents the current value (pA) of the current $I_c$ corresponding to the voltage level of the measurement signal $S_{esc}$. FIG. 7 shows the relation between the mass concentration and the measurement signal for the three sets of conditions under which particulates S have different particle diameter peak values. As in the case of FIG. 5, the particle diameter peak values of particulates S under the three sets of conditions are 75 nm, 87 nm, and 97 nm, respectively. For each of the three sets of conditions, FIG. 7 shows a linear approximation equation of y=a·x for measurement points obtained under each set of conditions and its correlation coefficient R$^2$. Notably, in general, the greater the correlation coefficient R$^2$ (namely, the greater the closeness to 1), the greater the degree of correlation.

As described above, in the particulate measurement system 10 of the present embodiment, the amount of particulates contained in the exhaust gas is determined on the basis of the measurement signal $S_{esc}$. However, as can be understood from FIG. 7, when the particle diameter peak value of particulates S changes, the relation between the mass concentration and the measurement signal changes. In view of this, in the present embodiment, the measurement signal $S_{esc}$ is corrected on the basis of the particle diameter of particulates S, whereby the influence of the difference of the particle diameter peak value on the relation between the measurement signal $S_{esc}$ and the mass concentration of particulates S (a measurement error caused by the influence of the difference of the particle diameter peak value) is reduced.

Incidentally, it is considered that the particle diameters of particulates S contained in the exhaust gas discharged from the internal combustion engine 400 fall within the range of 10 nm to 300 nm. In general, when a particulate S having a particle diameter which falls within that range is electrified through collision with the positive ions PI, the particulate S has a number of charges which is approximately proportional to its particle diameter, and its constant of proportionality can be considered to be 1. Therefore, for example, when the particle diameter of a certain particulate is two times the particle diameter of a different particulate, the number of charges of the certain particulate becomes two times the number of charges of the different particulate. Notably, when the particle diameter of a certain particulate is two times the particle diameter of a different particulate, the mass of the certain particulate becomes eight times the mass of the different particulate. As described above, the particle diameters of particulates S have a predetermined distribution; however, in the following description, "the particle diameter of particulates S" means the particle diameter peak value of particulates S.

In the present embodiment, when the mass concentration of particulates S is determined, correction of the measurement signal $S_{esc}$ is performed in accordance with the following expression (4).

$$y = y_0 \times (B/A)^N \quad (4)$$

In the expression (4), y represents a corrected measurement signal $S_{esc}$, $y_0$ represents an uncorrected measurement signal $S_{esc}$, A represents a particle diameter peak value which serves as a reference, B represents an estimated particle diameter peak value, and N represents an integer of 2 or greater (N=2 in the present embodiment). The particle diameter peak value serving as a reference is set in advance by a user. When the corrected measurement signal $S_{esc}$ is obtained, the mass concentration of particulates S is determined through use of the corrected measurement signal $S_{esc}$ and the above-described map or relational expression. The map or relational expression (a map showing the above-described relation between the voltage value of the measurement signal $S_{esc}$ and the amount of particulates contained in the exhaust gas or a relational expression showing the relation) used at that time is a map or a relational expression which is obtained when the exhaust gas contains particulates whose particle diameter peak value is equal to the particle diameter peak value serving as a reference (hereinafter, such particulates will be referred to as "reference particulates").

The mass of particulates S having the estimated particle diameter peak value is (B/A)$^3$ times the mass of the reference particulates. Meanwhile, since the number of charges of each of the particulates S having the estimated particle diameter peak value is B/A times the number of charges of each of the reference particulates, the uncorrected measurement signal $S_{esc}$ becomes B/A times the measurement signal $S_{esc}$ which is output when the exhaust gas contains the reference particulates. Therefore, the ratio of the uncorrected measurement signal $S_{esc}$ for the particulates S having the estimated particle diameter peak value to that for the reference particulates becomes (B/A)$^{-2}$ times the particulate mass ratio. In view of this, in the present embodiment, the measurement error due to the difference of the particle diameter peak value, which error is involved in the relation between the measurement signal $S_{esc}$ and the mass concentration of particulates S, is reduced by multiplying the measurement signal $S_{esc}$ (the measurement signal $S_{esc}$ in the case where the exhaust gas contains particulates S having the estimated particle diameter peak value) by (B/A)$^2$.

Figure 8:
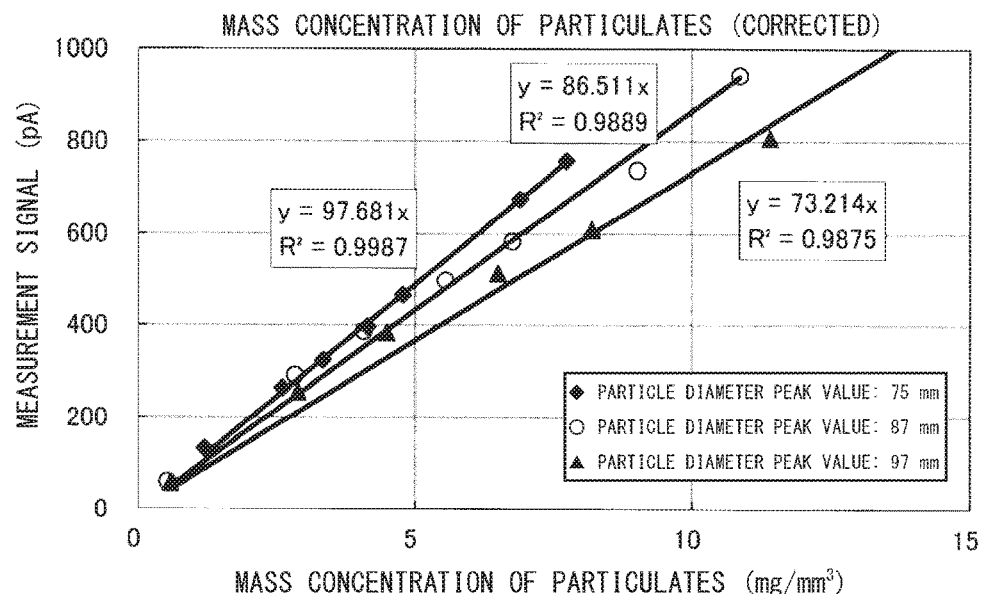
FIG. 8 is a graph showing the results of correction performed on the data of FIG. 7 in accordance with the above-mentioned expression (4).

FIG. 8 is a graph showing the results of correction performed on the data of FIG. 7 in accordance with the above-mentioned expression (4). FIG. 8 shows the results of correction performed for the case where the reference particle diameter peak value is 75 nm and the estimated particle diameter peak values are 87 nm and 97 nm. As can be seen from FIG. 8, this correction reduces the measurement error due to the difference of the particle diameter peak value, which error is involved in the relation between the measurement signal $S_{esc}$ and the mass concentration of particulates S. In this manner, the measurement accuracy of the mass concentration of particulates S can be improved by performing the correction in accordance with the above-mentioned expression (4).

A-4-2. Correction of Number Concentration of Particulates

Figure 9:
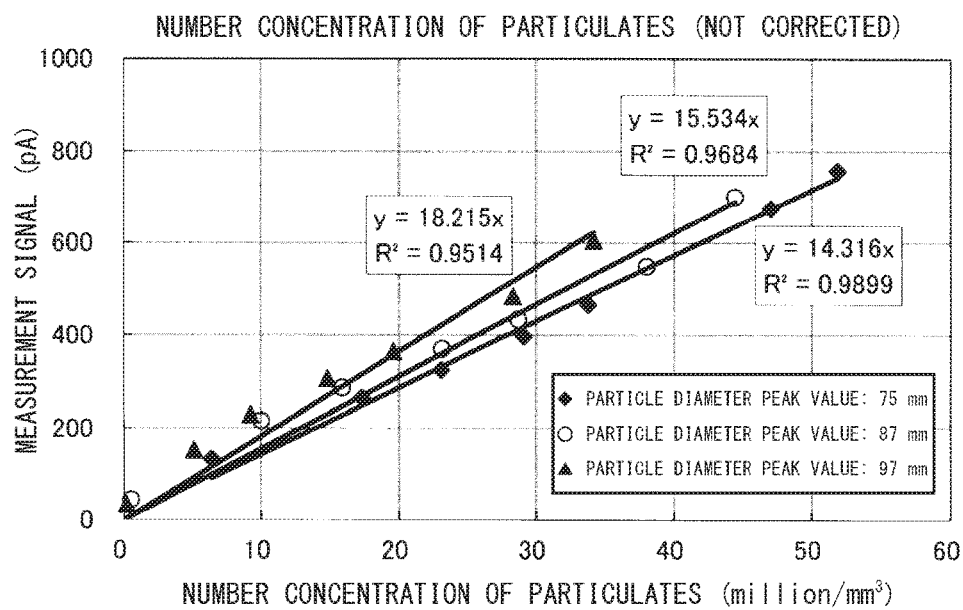
FIG. 9 is a graph showing an example of the relation between the measurement signal and the number concentration of particulates S contained in exhaust gas.

FIG. 9 is a graph showing an example of the relation between the measurement signal and the number concentration of particulates S contained in exhaust gas. The horizontal axis represents the number concentration (million/m$^3$) of particulates S contained in the exhaust gas, and the vertical axis represents the measurement signal $S_{esc}$. To be precise, the vertical axis represents the current value (pA) of the current $I_c$ corresponding to the voltage level of the measurement signal $S_{esc}$. FIG. 9 shows the relation between the number concentration and the measurement signal for the three sets of conditions under which particulates S have different particle diameter peak values. As in the case of FIG. 5, the particle diameter peak values of particulates S under the three sets of conditions are 75 nm, 87 nm, and 97 nm, respectively. For each of the three sets of conditions, FIG. 9 shows a linear approximation equation of y=a·x for measurement points obtained under each set of conditions and its correlation coefficient $R^2$. As can be understood from FIG. 9, when the particle diameter peak value of particulates S changes, the relation between the number concentration and the measurement signal changes, as in the case of the above-described mass concentration.

In the present embodiment, when the number concentration of particulates S is determined, correction of the measurement signal $S_{esc}$ is performed in accordance with the following expression (5).

$$y = y_0 \times (A/B) \tag{5}$$

In the expression (5), y represents a corrected measurement signal $S_{esc}$, $y_0$ represents an uncorrected measurement signal $S_{esc}$, A represents a particle diameter peak value which serves as a reference, and B represents an estimated particle diameter peak value. The particle diameter peak value serving as a reference is the same as the particle diameter peak value serving as a reference in the above-mentioned expression (4). When the corrected measurement signal $S_{esc}$ is obtained, the number concentration of particulates S is determined through use of the corrected measurement signal $S_{esc}$ and the above-described map or relational expression.

As described above, since the number of charges of each of particulates S having the estimated particle diameter peak value is B/A times the number of charges of each of the reference particulates, the uncorrected measurement signal $S_{esc}$ becomes B/A times the measurement signal $S_{esc}$ which is output when the exhaust gas contains the reference particulates. Therefore, the ratio of the uncorrected measurement signal $S_{esc}$ for the particulates S having the estimated particle diameter peak value to that for the reference particulates becomes B/A times the particulate number ratio. In view of this, in the present embodiment, the measurement error due to the difference of the particle diameter peak value, which error is involved in the relation between the measurement signal $S_{esc}$ and the number concentration of particulates S, is reduced by multiplying the measurement signal $S_{esc}$ by A/B which is the reciprocal of B/A.

Figure 10:
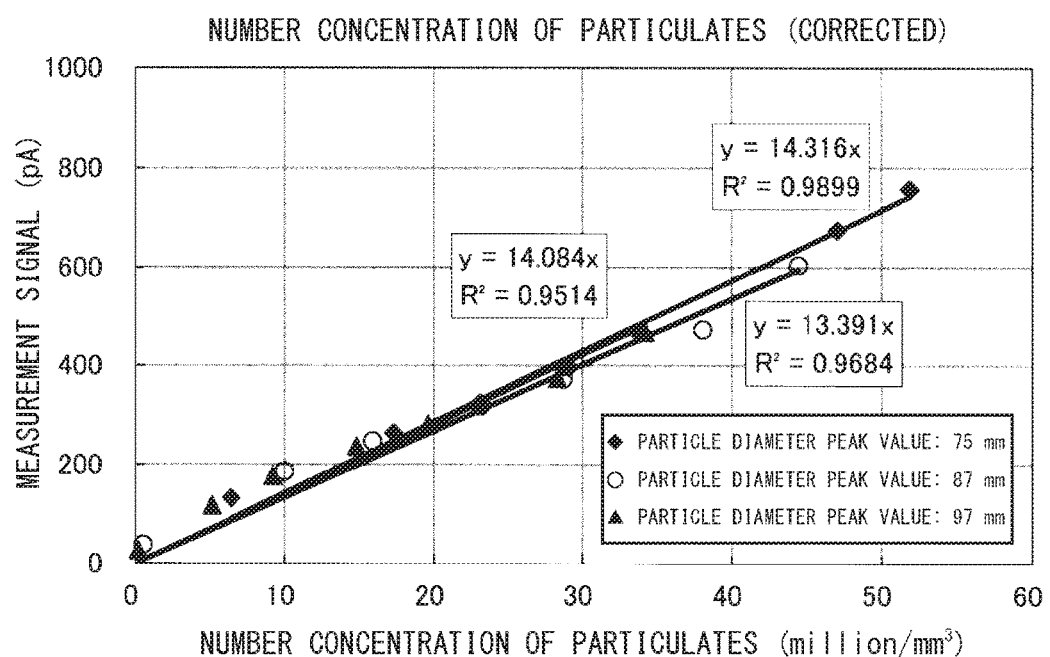
FIG. 10 is a graph showing the results of correction performed on the data of FIG. 9 in accordance with the above-mentioned expression (5).

FIG. 10 is a graph showing the results of correction performed on the data of FIG. 9 in accordance with the above-mentioned expression (5). FIG. 10 shows the results of correction performed for the case where the reference particle diameter peak value is 75 nm and the estimated particle diameter peak values are 87 nm and 97 nm. As can be seen from FIG. 10, this correction reduces the measurement error due to the difference of the particle diameter peak value, which error is involved in the relation between the measurement signal $S_{esc}$ and the number concentration of particulates S. In this manner, the measurement accuracy of the number concentration of particulates S can be improved by performing correction in accordance with the above-mentioned expression (5).

A-5. Particulate Amount Determination Processing

Figure 11:
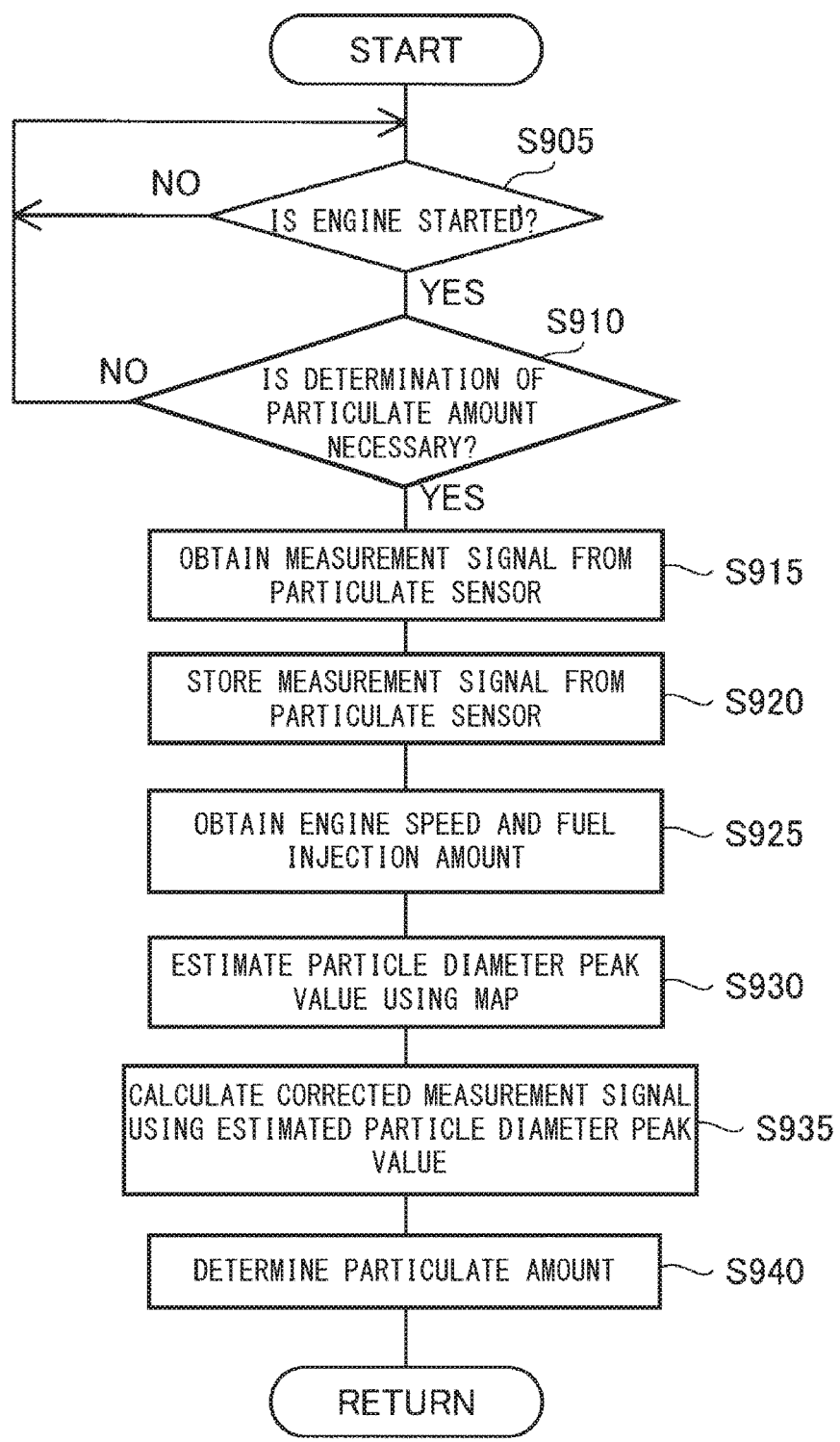
FIG. 11 is a flowchart showing the steps of particulate amount determination processing.

A method of determining the amount of particulates through the above-described correction of the measurement signal $S_{esc}$ will be described with reference to FIG. 11. FIG. 11 is a flowchart showing the steps of the particulate amount determination processing. In the particulate measurement system 10, when the ignition switch of the vehicle 500 is turned on, the sensor control section 600 executes the particulate amount determination processing. The sensor control section 600 waits until the internal combustion engine 400 is started (step S905). When the internal combustion engine 400 is started (step S905: YES), the sensor control section 600 judges whether or not determination of the amount of particulates is necessary (step S910). In the case where the sensor control section 600 judges that determination of the amount of particulates is unnecessary (step S910: NO), the sensor control section 600 returns to step S905.

In contrast, in the case where the sensor control section 600 judges that determination of the amount of particulates is necessary (step S910: YES), the particulate amount determination section 610 obtains the measurement signal $S_{esc}$ from the particulate sensor 100 (step S915) and stores the measurement signal $S_{esc}$ (step S920). The particle diameter estimation section 620 obtains the rotational speed of the internal combustion engine 400 and the fuel injection amount by receiving the signals from the sensors 406 (step S925). The particle diameter estimation section 620 estimates the particle diameter peak value of particulates S by referring to the map (step S930). The particulate amount determination section 610 corrects the measurement signal $S_{esc}$, by the above-described method, through use of the particle diameter peak value of particulates S estimated by the particle diameter estimation section 620 (step S935). The particulate amount determination section 610 determines the particulate amount (the mass concentration and number concentration of particulates S) on the basis of the corrected measurement signal $S_{esc}$ (step S940). After having determined the particulate amount, the sensor control section 600 returns to the above-described step S905.

In the above-described particulate measurement system 10 of the present embodiment, the particle diameter peak value of particulates S contained in the exhaust gas is estimated, and the measurement signal $S_{esc}$ is corrected by multiplying the measurement signal $S_{esc}$ by a coefficient ($(B/A)^N$ (N=2 in the present embodiment) or A/B) relating to the ratio between the estimated particle diameter peak value and the reference particle diameter peak value. Therefore, the measurement error due to the difference of the particle diameter peak value can be reduced, whereby the measurement accuracy of the particulate amount can be improved. Also, since the particle diameter peak value is estimated on the basis of two types of parameters relating to drive of the internal combustion engine 400 (the rotational speed of the internal combustion engine 400 and the fuel injection amount), the estimation accuracy of the particle diameter peak value can be increased as compared with a configuration in which the particle diameter peak value is estimated on the basis of a single type of parameter, whereby the measurement accuracy of the particulate amount can be improved. Also, since the rotational speed of the internal combustion engine 400 and the fuel injection amount are considered to be particularly influential on the particle diameter of particulates S contained in the exhaust gas, through use of these parameters, the estimation accuracy of the particle diameter peak value is increased, and the measurement accuracy of the particulate amount can be improved. Furthermore, since the particle diameter peak value is used as the particle diameter of particulates S, the map for estimating the particle diameter can be readily configured. Also, since the accuracy in measuring the amount of particulates contained in the exhaust gas discharged from the internal combustion engine 400 of the vehicle 500 can be improved, deterioration and/or anomaly of a filter apparatus for trapping the particulates contained in the exhaust gas can be detected accurately.

B. Modifications

The present invention is not limited to the above-described embodiment, and can be implemented in various forms without departing from the scope of the invention. For example, the following modifications are possible.

B-1. Modification 1

The configuration of the particulate measurement system 10 described in the embodiment is an example, and the present invention can be realized by a configuration other than that of the particulate measurement system 10 shown in the embodiment. For example, the particulate measurement system 10 is not required to have the second electrode 132. Also, the particulate measurement system 10 may be configured such that the ion generation section 110 is provided separately from the particulate sensor 100 rather than being provided inside the particulate sensor 100. Further, the first electrode 112 may be disposed in the electrification chamber 121 such that the first electrode 112 penetrates the partition wall 42, whereby corona discharge is produced between a forward end portion of the first electrode 112 and the inner wall surface of the electrification chamber 121. In this case, the ion generation section 110 and the exhaust gas electrification section 120 are united together. Also, the measurement signal generation circuit 740 may have any of various configurations other than the configuration described in the embodiment so long as the measurement signal generation circuit 740 can generate a signal representing the amount of particulates.

B-2. Modification 2

The particulate measurement system 10 of the above-described embodiment is configured to generate positive ions between the first electrode 112 and the partition wall 42 by means of corona discharge. However, the particulate measurement system 10 may be configured to generate negative ions by means of corona discharge.

B-3. Modification 3

In the embodiment, the measurement signal $S_{esc}$ is corrected. However, instead of the measurement signal $S_{esc}$, the mass concentration and number concentration of particulates S which are determined on the basis of the measurement signal $S_{esc}$ may be corrected. In this case as well, the above-mentioned expression (4) can be used as a correction expression in which y represents the corrected mass concentration of particulates S and $y_0$ represents the uncorrected mass concentration of particulates S. Similarly, the above-mentioned expression (5) can be used as a correction expression in which y represents the corrected number concentration of particulates S and $y_0$ represents the uncorrected number concentration of particulates S. In this case as well, the measurement accuracy of the particulate amount can be improved through simple correction. Also, in the present embodiment, N in the expression (4) is 2. However, depending on, for example, the environment in which the particulate sensor 100 is used, an integer larger than 2 may be used as the value of N so as to improve the measurement accuracy of the mass concentration of particulates.

B-4. Modification 4

In the embodiment, the particle diameter peak value of particulates S is estimated on the basis of the parameters representing the rotational speed of the internal combustion engine 400 and the fuel injection amount. However, the present invention is not limited thereto. In place of the rotational speed of the internal combustion engine 400 and the fuel injection amount, other operating conditions, such as the speed of the vehicle 500, the torque of the internal combustion engine 400, the exhaust pressure of the internal combustion engine 400, the intake pressure of the internal combustion engine 400, the EGR opening degree, the amount of air taken into the internal combustion engine 400, the ignition timing, may be used. Also, in stead of the operating condition parameters, an environmental parameter which changes with operation of the internal combustion engine 400 (the exhaust gas temperature of the internal combustion engine 400, etc.) may be used. This is because these parameters are considered to influence the particle diameter of particulates S contained in the exhaust gas. Also, in the embodiment, the particle diameter peak value of particulates S is estimated on the basis of two types of parameters. However, the particle diameter peak value of particulates S may be estimated on the basis of a single type of parameter or three or more types of parameters.

B-5. Modification 5

In the embodiment, the particle diameter peak value of particulates S is used as the particle diameter used for determination of the particulate amount. However, instead of the particle diameter peak value, the average of the particle diameters of particulates S may be used. Even in the case of a configuration which uses the average of the particle diameters of particulates S, the map for estimating the particle diameter can be readily configured. In this case, the average of the particle diameters of particulates S corresponds to the particle diameter in claims.

B-6. Modification 6

In the embodiment, the particulate measurement system 10 is mounted on the vehicle 500 and measures the amount of particulates contained in the exhaust gas discharged from the internal combustion engine 400. However, the present invention is not limited thereto. Particulates contained in exhaust gas discharged from each of other arbitrary internal combustion engines such as an internal combustion engine mounted on an arbitrary moving body (e.g., a ship) and a stationary internal combustion engine may be measured. Also, the amount of particulates contained in smoke within a chimney of a plant may be measured, and the amount of soot or other arbitrary particulates contained in a certain space may be measured for the purpose of monitoring the environment within an office or the environment of a road.

DESCRIPTION OF REFERENCE NUMERALS AND SYMBOLS

10 . . . particulate measurement system
31 . . . gas flow passage
35 . . . discharge hole
41 . . . nozzle
42 . . . partition wall
45 . . . inflow hole
100 . . . particulate sensor
110 . . . ion generation section
111 . . . ion generation chamber
112 . . . first electrode
120 . . . exhaust gas electrification section
121 . . . electrification chamber 130 . . . ion trapping section
131 . . . trapping chamber
132 . . . second electrode
221 . . . first wiring line
222 . . . second wiring line
223 . . . signal line
230 . . . shunt resistor
300 . . . sensor drive section
400 . . . internal combustion engine
402 . . . exhaust gas pipe
405 . . . fuel pipe
410 . . . filter apparatus
420 . . . vehicle control section
430 . . . fuel supply section
500 . . . vehicle
600 . . . sensor control section
610 . . . particulate amount determination section
620 . . . particle diameter estimation section
700 . . . electric circuit section
S . . . particulate

The invention claimed is:

1. A particulate measurement system comprising:

an ion generation section for generating ions by means of corona discharge;

an electrification chamber for electrifying, by using the ions, at least a portion of particulates contained in a gas under measurement;

an ion trapping section for trapping at least a portion of the ions which have not been used for the electrification of the particulates;

a measurement signal generation circuit for generating a measurement signal which correlates with the amount of the particulates contained in the gas under measurement on the basis of a current value corresponding to a difference between the amount of the ions generated from the ion generation section and the amount of the ions captured by the ion trapping section; and a particulate amount determination section for determining the amount of the particulates contained in the gas under measurement on the basis of the measurement signal, the particulate measurement system being characterized by further comprising:

a particle diameter estimation section for estimating the particle diameter of the particulates contained in the gas under measurement, wherein the particulate amount determination section performs correction by multiplying the measurement signal or the amount of the particulates determined from the measurement signal by a coefficient relating to a ratio between the estimated particle diameter and a reference particle diameter, and wherein (i) the particulate amount determination section determines, as the amount of the particulates, the mass concentration of the particulates by performing the correction in accordance with an expression of $y=y_0 \times (B/A)^N$, where y is the measurement signal or the mass concentration of the particulates after the correction, $y_0$ is the measurement signal or the mass concentration of the particulates before the correction, A is the reference particle diameter, B is the estimated particle diameter, and N is an integer of 2 or greater, or (ii) the particulate amount determination section determines, as the amount of the particulates, the number concentration of the particulates by performing the correction in accordance with an expression of $y=y_0 \times (A/B)$, where y is the measurement signal or the number concentration of the particulates after the correction, $y_0$ is the measurement signal or the number concentration of the particulates before the correction, A is the reference particle diameter, and B is the estimated particle diameter.

2. A particulate measurement system as claimed in claim 1, wherein the particulate measurement system measures the amount of the particulates contained in exhaust gas discharged from an internal combustion engine of a vehicle.

3. A particulate measurement system as claimed in claim 2, wherein the particle diameter estimation section estimates the particle diameter on the basis of a parameter relating to drive of the internal combustion engine.

4. A particulate measurement system as claimed in claim 3, wherein the particle diameter estimation section estimates the particle diameter on the basis of a plurality of parameters different from one another.

5. A particulate measurement system as claimed in claim 4, wherein the plurality of parameters different from one another include at least rotational speed of the internal combustion engine and fuel injection amount.

* * * * *